(12) United States Patent  
MacGillivray

(10) Patent No.: US 7,772,416 B2  
(45) Date of Patent: Aug. 10, 2010

(54) DATA STORAGE MATERIALS

(75) Inventor: Leonard R. MacGillivray, Iowa City, IA (US)

(73) Assignee: University of Iowa Research Foundation, Iowa City, IA (US)

( * ) Notice: Subject to any disclaimer, the term of this patent is extended or adjusted under 35 U.S.C. 154(b) by 1261 days.

(21) Appl. No.: 11/150,587

(22) Filed: Jun. 10, 2005

(65) Prior Publication Data

US 2006/0004217 A1   Jan. 5, 2006

Related U.S. Application Data

(60) Provisional application No. 60/578,781, filed on Jun. 10, 2004.

(51) Int. Cl.  
*C07F 3/06* (2006.01)  
*C07F 15/00* (2006.01)

(52) U.S. Cl. .................................. 556/32; 556/135

(58) Field of Classification Search .................. 556/32, 556/135  
See application file for complete search history.

(56) References Cited

U.S. PATENT DOCUMENTS

2004/0014963 A1   1/2004   Atwood et al.

FOREIGN PATENT DOCUMENTS

| WO | WO 99/16734    | 4/1999  |
| WO | WO 00/63140    | 10/2000 |
| WO | WO 2004/042270 | 5/2004  |
| WO | WO 2005/035473 | 4/2005  |
| WO | WO 2005/124754 | 12/2005 |

OTHER PUBLICATIONS

Pascu et al., Polyhedron, vol. 23, pp. 673-678 (2004).*  
International Search Report for International Application No. PCT/US2005/020599, mailed Dec. 6, 2005.  
Papaefstathiou et al., "An inverted metal-organic framework with compartmentalized cavities constructed by using an organic bridging unit derived from the solid state", *Angew Chem Int Ed*, 41(12), 2070-2073 (2002).  
International Search Report for International U.S. Appl. No. PCT/US2004/033295, mailed Apr. 21, 2005.  
Anderson et al., "Templates in Organic Synthesis: Definitions and Roles", F. Diederich, P. S. Stang, Eds.: Wiley-VCH, New York, 1-38 (2000).  
Atwood et al., "Storage of Methane and Freon by Interstitial van der Waals Confinement", *Science*, 296, 2367-2369 (2002).  
Balzani et al., "The Bottom-Up Approach to Molecular-Level Devices and Machines", *Chem. Eur. J.*, 8, 5524-5532 (2002).  
Bassani et al., "Supramolecular Catalysis of Olefin [2+2] Photodimerization", *J. Am. Chem. Soc.*, 122, 8795-8796 (2000).  
Damste et al., "Linearly Concatenated Cyclobutane Lipids Form a Dense Bacterial Membrane", *Nature*, 419, 708-712 (2002).  
Delong, "All in the Packaging", *Nature*, 419, 676-677 (2002).  
Desiraju, "Crystal Gazing: Structure Prediction and Polymorphism", *Science*, 278, 404-405 (1997).  
Drexler, "Molecular Engineering: An Approach to the Development of General Capabilities for Molecular Manipulation", *PNAS*, 78, 5275-5278 (1981).

(Continued)

*Primary Examiner*—Porfirio Nazario Gonzalez  
(74) *Attorney, Agent, or Firm*—Viksnins Harris & Padys PLLP

(57) ABSTRACT

The invention provides metal-organic complexes useful for storing information in an information storage system. The invention also provides methods for forming such complexes on a substrate, as well as apparatuses and systems comprising such complexes.

7 Claims, 12 Drawing Sheets

OTHER PUBLICATIONS

Drexler, "Machine-Phase Nanotechnology", *Sci. Amer.*, 285, 74-75 (2001).

Eigler et al., "Positioning Single Atoms with a Scanning Tunnelling Microscope", *Nature*, 344, 524-526 (1990).

Friščič et al., "Double Inclusion of Ferrocene within a Doubly Inter-penetrated Three-Dimensional Framework Based on a Resorcin[4]arene", *J. Organometallic Chemistry*, 666, 43-48 (2003).

Friščič et al., "Template-switching: A Supramolecular Strategy for the Quantitative, Gram-Scale Construction of a Molecular Target in the Solid State", *Chem. Comm.*, 1306-1307 (2003).

Friščič et al., "Cyclophanes and Ladderanes: Molecular Targets for Supramolecular Chemists", *Supramolecular Chemistry*, 17, 47-51 (2005).

Gao et al., "Supramolecular Construction of Molecular Ladders in the Solid State", *Angew. Chem, Int. Ed.*, 43, 232-236 (2004).

Hamilton et al., "Discrete and Infinite Coordination Arrays Derived from a Template-Directed, Solid-State, Organic Synthesis", *CrystEngComm.*, 4, 223-226 (2002).

Hamilton et al., "A Polyhedral Host Constructed Using a Linear Template", *J. Am. Chem. Soc.*, 124, 11606-11607 (2002).

Hecht, "Welding, Organizing, and Planting Organic Molecules on Substrate Surfaces—Promising Approaches Towards Nanoarchitectonics from the Bottom up", *Angew. Chem. Int. Ed. Engl.*, 42, 24-26 (2003).

Hla et al., "Inducing Single-Molecule Chemical Reactions with a UHV-STM: A New Dimension for Nano-Science and Technology", *ChemPhysChem.*, 2, 361-366 (2001).

Hopf et al., "Topochemical Reaction Control in Solution", *Angew. Int. Ed. Engl.*, 34, 685-687 (1995).

Hopf, "Step by Step—From Nonnatural to Biological Molecular Ladders", *Angew. Chem. Int. Ed.*, 42, 2822-2825 (2003).

Kelly et al., "A Bisubstrate Reaction Template", *J. Am. Chem. Soc.*, 111, 3744-3745 (1989).

Kuypers et al., "Anaerobic Ammonium Oxidation by Anammox Bacteria in the Black Sea", *Nature*, 422, 608-611 (2003).

Li et al., "Synthesis, Characterization, and Photophysics Studies of Photoactive Chromophore 2-Naphthyl-Labeled [n]-Ladderanes" *J. Am. Chem. Soc.*, 118, 11752-11758 (1996).

Lindoy et al., "Mono- and Diformylation of 4-Substituted Phenols: A New Application of the Duff Reaction", *Synthesis*, 1029-1032 (1998).

MacGillivray, "From Engineering Crystals to Engineering Molecules: Emergent Consequences of Controlling Reactivity in the Solid State Using Linear Templates", *CrystEngComm.*, 4, 37-41 (2002).

MacGillivray, "Controlling Molecular Synthesis in the Solid State Using Linear Templates", in *"Strength from Weakness: Structural Consequences of Weak Interactions in Molecular, Supermolecules, and Crystals"* Eds A Domenicano and I Hargittai, 355-365 (2002).

MacGillivray et al., "Toward a Reactant Library in Template-Directed Solid-State Organic Synthesis: Reactivity Involving a Monofunctional Reactant Based on a Stilbazole", *Ind. Eng. Chem. Res.*, 41, 4494-4497 (2002).

MacGillivray, "Supramolecular Control of Reactivity in the Solid State Using Linear Templates", in *Separations and Reactions in Organic Supramolecular Chemistry*, Eds F. Toda and R. Bishop, 185-204 (2004).

MacGillivray et al., "Template-Controlled Synthesis in the Solid-State", *Topics in Current Chemistry*, 248, 201-221 (2004).

Mehta et al., "Characterization of [n]-Ladderanes of Unprecedented Length: A New Record for Fused Carbocyclic Arrays", *J. Org. Chem.*, 59, 6131-6132 (1994).

Nicolaou et al., "The Art and Science of Total Synthesis at the Dawn of the Twenty-First Century", *Angew. Chem. Int. Ed.*, 39, 44-122 (2000).

Papaefstathiou et al., "Inverted Metal-Organic Frameworks: Solid-State Hosts with Modular Functionality", *Coordinated Chemistry Reviews*, 246, 169-184 (2003).

Papaefstathiou et al., "Directed Assembly and Reactivity of Olefins within a One-Dimensional Ladder-Like Coordination Polymer Based on a Dinuclear Zn(II) Platform", *Chem Commun.*, 3974-3976 (2005).

Rekharsky et al., "Ion-Pairing Molecular Recognition in Water: Aggregation at Low Concentrations that is Entropy-Driven", *J. Am. Chem. Soc.*, 124, 14959-14967 (2002).

Schmidt, "Photodimerization in the Solid State", *Pure Appl. Chem.*, 27, 647-678 (1971).

Warrener et al., "A Tandem Cycloaddition Protocol for the Controlled Synthesis of [n]Ladderanes: New Rods and Spacers", *J. Am. Chem. Soc.*, 116, 3645-3646 (1994).

Whitesides, "The Once and Future Nanomachine", *Sci. Amer.*, 285, 78-83 (2001).

Williams et al., "How Can Enzymes be so Efficient?", *Chem. Commun.*, 1973-1976 (2003).

\* cited by examiner

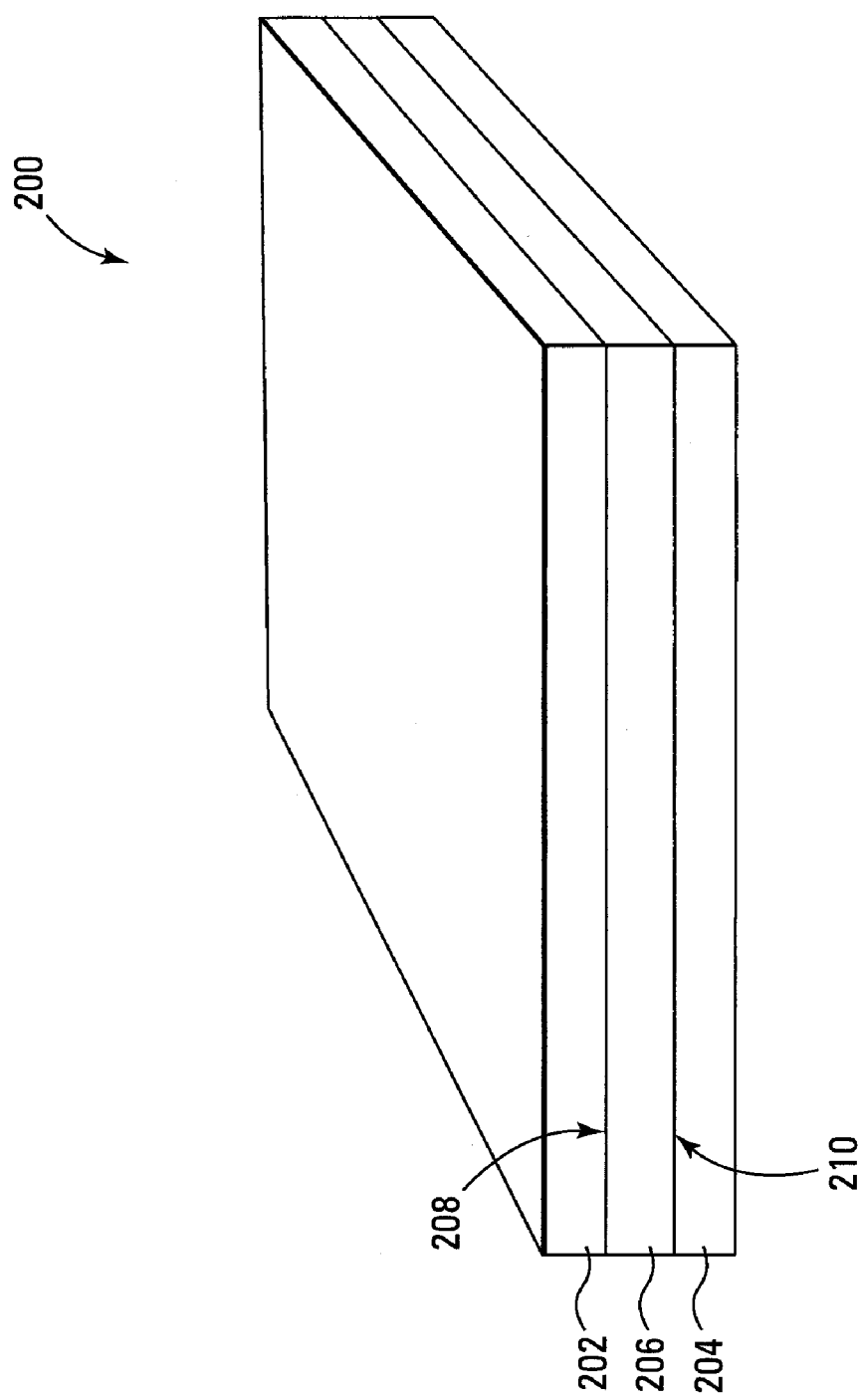

DATA STORAGE MATERIALS

PRIORITY OF INVENTION

This application claims priority to U.S. Provisional Patent Application No. 60/578,781, filed Jun. 10, 2004; and to International Patent Application Number PCT/US2004/033295, filed 8 Oct. 2004.

GOVERNMENT FUNDING

The invention described herein was made with United States Government support under CAREER Award, L.R.M., DMR-0133138 awarded by the National Science Foundation. The United States Government may have certain rights in the invention.

BACKGROUND OF THE INVENTION

Information storage systems include magnetic, electronic, and optical methods of storing information. As the demand for higher density information storage continues, the demand for optical storage on traditionally electronic substrates, such as semiconductors, and other media will increase. The density of current optical information storage systems, such as systems for storing information on a compact disk or a video disk cannot be easily increased and migrated to integrated circuit substrates or other high density media.

SUMMARY OF THE INVENTION

The invention provides materials that can be incorporated into information storage systems due to their physical properties (e.g. their optical properties).

In one embodiment the invention provides a metal-organic coordination complex of the invention that comprises two or more metal atoms wherein one metal atom is associated with a first organic group comprising one or more double bonds and another metal atom is associated with a second organic group comprising one or more double bonds such that one or more double bonds in the first organic group are spatially oriented to react (e.g. by cyclization) with one or more double bonds in the second organic group. In another embodiment the invention provides a method comprising, treating such a complex with light, heat, electric current, or a combination thereof, so that one or more double bonds in one organic group react with one or more double bonds in another organic group to form one or more cyclobutane rings. In another embodiment the invention provides a material (e.g. a solid-state material) prepared according to such a method.

In another embodiment the invention provides an metal-organic coordination complex of the invention comprising two or more metal atoms having a first organic group associated with one metal atom and a second organic group associated with another metal atom, wherein two carbon atoms of the first organic group and two carbon atoms of the second organic group form a cyclobutane ring.

In another embodiment the invention provides a method comprising: forming a complex of the invention (e.g. as a film) on a substrate.

In another embodiment the invention provides a method comprising: forming a film of a complex of the invention on a substrate; and irradiating the complex to form a material having a plurality of characteristic fluorescent energies.

In another embodiment the invention provides an apparatus comprising: a substrate; and a complex of the invention formed on the substrate.

In another embodiment the invention provides an apparatus comprising: a first translucent material; a second translucent material; and a film including a complex of the invention formed between the first translucent material and the second translucent material.

In another embodiment the invention provides an apparatus comprising: a radiation source; a complex of the invention to receive radiation from the radiation source; and a radiation detector to detect radiation emitted from the complex.

In another embodiment the invention provides an apparatus comprising: a substrate; a first complex of the invention formed on the substrate, the complex tuned to fluoresce at a first energy; and a second complex of the invention formed on the first complex, the second complex tuned to fluoresce at a second energy, the second energy being different from the first energy.

In another embodiment the invention also provides a system comprising: a processor; a radiation source coupled to the processor; a complex of the invention formed on a substrate to receive radiation from the radiation source; and a radiation detector coupled to the processor, the radiation detector to detect radiation emitted from the complex.

BRIEF DESCRIPTION OF THE FIGURES

The patent application file contains at least one drawing executed in color. Copies of this patent or patent application publication with color drawings will be provided by the office upon request and payment of the necessary fee.

FIG. 2A is a perspective view of an apparatus including a first translucent material, a second translucent material, and a film including a complex of the invention formed between the first translucent material and the second translucent material in accordance with some embodiments of the invention.

DETAILED DESCRIPTION OF THE INVENTION

Figure 1:
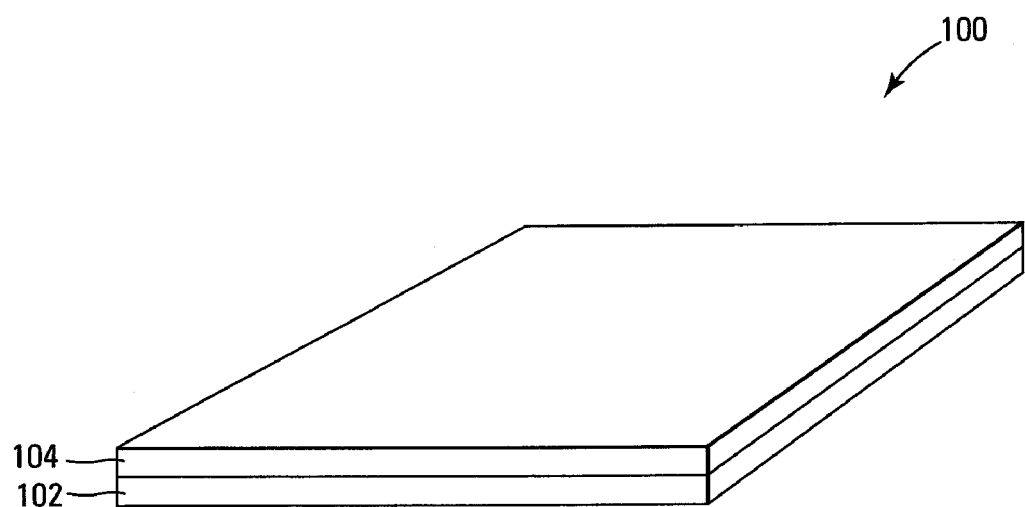
FIG. 1 is a perspective view of an apparatus including a substrate and a complex of the invention formed on the substrate in accordance with some embodiments of the invention.

The following definitions are used, unless otherwise described. Halo is fluoro, chloro, bromo, or iodo. Alkyl, alkoxy, etc. denote both straight and branched groups; but reference to an individual radical such as propyl embraces only the straight chain radical, a branched chain isomer such as isopropyl being specifically referred to. Aryl denotes a phenyl radical or an ortho-fused bicyclic carbocyclic radical having about nine to ten ring atoms in which at least one ring is aromatic. Heteroaryl encompasses a radical attached via a ring carbon of a monocyclic aromatic ring containing five or six ring atoms consisting of carbon and one to four heteroatoms each selected from the group consisting of non-peroxide oxygen, sulfur, and N(X) wherein X is absent or is H, O, $(C_1-C_4)$alkyl, phenyl or benzyl, as well as a radical of an ortho-fused bicyclic heterocycle of about eight to ten ring atoms derived therefrom, particularly a benz-derivative or one derived by fusing a propylene, trimethylene, or tetramethylene diradical thereto.

Specific and preferred values listed below for radicals, substituents, and ranges, are for illustration only; they do not exclude other defined values or other values within defined ranges for the radicals and substituents Specifically, $(C_1-C_6)$alkyl can be methyl, ethyl, propyl, isopropyl, butyl, iso-butyl, sec-butyl, pentyl, 3-pentyl, or hexyl; $(C_1-C_6)$alkoxy can be methoxy, ethoxy, propoxy, isopropoxy, butoxy, iso-butoxy, sec-butoxy, pentoxy, 3-pentoxy, or hexyloxy; $(C_1-C_6)$alkanoyl can be acetyl, propanoyl or butanoyl; $(C_1-C_6)$alkoxycarbonyl can be methoxycarbonyl, ethoxycarbonyl, propoxycarbonyl, isopropoxycarbonyl, butoxycarbonyl, pentoxycarbonyl, or hexyloxycarbonyl; $(C_2-C_6)$alkanoyloxy can be acetoxy, propanoyloxy, butanoyloxy, isobutanoyloxy, pentanoyloxy, or hexanoyloxy; aryl can be phenyl, indenyl, or naphthyl; and heteroaryl can be furyl, imidazolyl, triazolyl, triazinyl, oxazoyl, isoxazoyl, thiazolyl, isothiazoyl, pyrazolyl, pyrrolyl, pyrazinyl, tetrazolyl, pyridyl, (or its N-oxide), thienyl, pyrimidinyl (or its N-oxide), indolyl, isoquinolyl (or its N-oxide) or quinolyl (or its N-oxide).

Specific Complexes of the Invention

In one specific embodiment of the invention, the complex of the invention can have following structure:

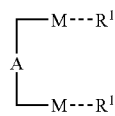

wherein:

the group MAM is a metal-organic group comprising at least two metal atoms M;

each $R^1$ is independently an organic group comprising one or more double bonds; and the dashed lines designate an association between $R^1$ and M.

In another specific embodiment of the invention, the complex of the invention can have following structure:

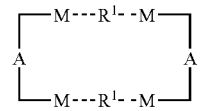

wherein:

each group MAM is independently a metal-organic group comprising at least two metal atoms M;

each $R^1$ is independently an organic group comprising one or more double bonds; and the dashed lines designate an association between $R^1$ and M.

In another specific embodiment of the invention, one or more of the groups MAM comprises 4 or more metal atoms.

In another specific embodiment of the invention, one or more of the groups MAM comprises 3 or more metal atoms.

In another specific embodiment of the invention, each of the groups MAM comprise only 2 metal atoms.

In another specific embodiment of the invention, one or more of the groups MAM is a Schiff-base complex.

In another specific embodiment of the invention, each group MAM is a Schiff-base complex.

In another specific embodiment of the invention, each group MAM is a dinuclear Schiff-base complex.

In another specific embodiment of the invention, the complex of the invention is a solid.

In another specific embodiment of the invention, the complex of the invention is a crystalline solid.

Specific Complexes of the Invention that Comprise One or More Cyclobutane Rings

In one specific embodiment of the invention, the complex of the invention comprises the following structure:

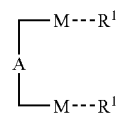

wherein:

the group MAM is an metal-organic group comprising at least two metal atoms M;

each $R^1$ is independently an organic group wherein two carbon atoms of the first organic group and two carbon atoms of the second organic group form a cyclobutane ring; and the dashed lines designate an association between $R^1$ and M.

In another specific embodiment of the invention, the complex of the invention comprises the following structure:

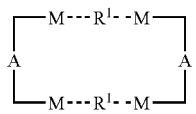

wherein:
each group MAM is independently a metal-organic group comprising at least two metal atoms M;
each $R^1$ is independently an organic group wherein two carbon atoms of the first organic group and two carbon atoms of the second organic group form a cyclobutane ring; and
the dashed lines designate an association between $R^1$ and M.

In one specific embodiment of the invention each metal atom is independently a transition metal atom.

In one specific embodiment of the invention, each metal atom is independently Sc, Ti, V, Cr, Mn, Fe, Co, Ni, Cu, Zn, Y, Zr, Nb, Mo, Tc, Ru, Rh, Pd, Ag, Cd, La, Hf, Ta, w, Re, Os, Ir, Pt, Au, or Hg.

In one specific embodiment of the invention, each metal atom is independently Sc, Ti, V, Cr, Mn, Fe, Co, Ni, Cu, or Zn.

In one specific embodiment of the invention, each metal atom is independently Y, Zr, Nb, Mo, Tc, Ru, Rh, Pd, Ag, or Cd.

In one specific embodiment of the invention, each metal atom is independently La, Hf, Ta, w, Re, Os, Ir, Pt, Au, or Hg.

In one specific embodiment of the invention, each metal atom is independently Zn.

In one specific embodiment of the invention, one or more of the groups MAM comprises 4 or more metal atoms.

In one specific embodiment of the invention, one or more of the groups MAM comprises 3 or more metal atoms.

In one specific embodiment of the invention, each of the groups MAM comprise only 2 metal atoms.

In one specific embodiment of the invention, one or more of the groups MAM is a Schiff-base complex.

In one specific embodiment of the invention, each group MAM is a Schiff-base complex.

In one specific embodiment of the invention, each group MAM is a dinuclear Schiff-base complex.

In one specific embodiment of the invention, one or more of the groups MAM has the following structure:

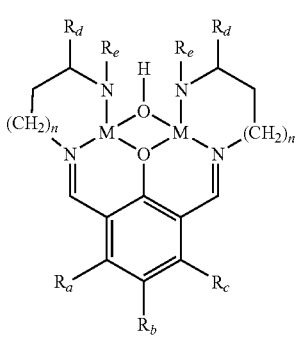

wherein:
each $R_a$, $R_b$, and $R_c$ is independently hydrogen, halo, nitro, cyano, $C_{1-6}$alkyl, $C_{1-6}$alkoxy, $C_{1-6}$alkanoyl, $C_{1-6}$alkanoyloxy, $C_{1-6}$alkoxycarbonyl, trifluoromethyl, (aryl)$C_{1-6}$alkyl, carboxy, or trifluoromethoxy;

each n is independently 0, 1, 2, or 3; and
each $R_d$ and $R_e$ is independently hydrogen or $C_{1-6}$alkyl; or $R_d$ and $R_e$ together with the atoms to which they are attached form a 5, 6, 7, or 8 membered saturated or unsaturated ring.

In one specific embodiment of the invention, one or more of the groups MAM has the following structure:

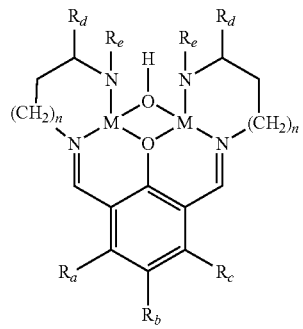

wherein:
each $R_a$, $R_b$, and $R_c$ is independently hydrogen, halo, nitro, cyano, $C_{1-6}$alkyl, $C_{1-6}$alkoxy, $C_{1-6}$alkanoyl, $C_{1-6}$alkanoyloxy, $C_{1-6}$alkoxycarbonyl, trifluoromethyl, or trifluoromethoxy;

each n is independently 0, 1, 2, or 3; and
each $R_d$ and $R_e$ is independently hydrogen or $C_{1-6}$alkyl; or $R_d$ and $R_e$ together with the atoms to which they are attached form a 5, 6, 7, or 8 membered saturated or unsaturated ring.

In one specific embodiment of the invention, $R_a$ is hydrogen.

In one specific embodiment of the invention, $R_b$ is hydrogen.

In one specific embodiment of the invention, $R_b$ is halo, nitro, cyano, $C_{1-6}$alkyl, $C_{1-6}$alkoxy, $C_{1-6}$alkanoyl, $C_{1-6}$alkanoyloxy, $C_{1-6}$alkoxycarbonyl, trifluoromethyl, or trifluoromethoxy.

In one specific embodiment of the invention $R_b$ is halo, $C_{1-6}$alkyl, benzyl, or $C_{1-6}$alkoxy.

In one specific embodiment of the invention, $R_c$ is hydrogen.

In one specific embodiment of the invention, each $R_d$ and $R_e$ is independently hydrogen or $C_{1-6}$alkyl.

In one specific embodiment of the invention, $R_d$ and $R_e$ together with the atoms to which they are attached form 5 or 6 membered saturated or unsaturated ring.

In one specific embodiment of the invention, $R_d$ and $R_e$ together with the atoms to which they are attached form a pyridine, pyrrole, pyrimidine, pyrazine, pyridazine, imidazole, pyrazole, pyrrolidine, piperidine, morpholine, piperazine, or azepine ring.

In one specific embodiment of the invention, $R_d$ and $R_e$ together with the atoms to which they are attached form a pyridine, pyrrole, imidazole, pyrrolidine, piperidine, or azepine ring.

In one specific embodiment of the invention, $R_d$ and $R_e$ together with the atoms to which they are attached form a pyridine ring.

In one specific embodiment of the invention, one or more of the groups MAM has the following structure:

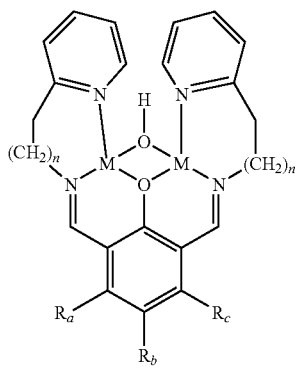

In one specific embodiment of the invention, each n is 1.

In one specific embodiment of the invention, each ---- designates association by coordination or by a covalent bond.

In one specific embodiment of the invention, each $R^1$ independently has the formula X—Y—X; wherein each X is independently hydrogen or a group that is capable of associating with a metal atom; and each Y is independently an organic group that forms one or more cyclobutane rings with another Y.

In one specific embodiment of the invention, each X is independently a group that is capable of associating with a metal atom.

In one specific embodiment of the invention, each X independently comprises an amino nitrogen, a thiol, an alcohol, or a carboxylic acid.

In one specific embodiment of the invention, each X is independently a pyridine ring.

In one specific embodiment of the invention, each X is a 4-pyridine ring.

In one specific embodiment of the invention, each Y forms 1-10 cyclobutane rings with another Y.

In one specific embodiment of the invention, each Y forms 1-5 cyclobutane rings with another Y.

In one specific embodiment of the invention, each Y forms one cyclobutane ring with another Y.

In one specific embodiment of the invention, the complex of the invention is a solid.

In one specific embodiment of the invention, the complex of the invention is a crystalline solid.

Metal-Organic Group

The complexes of the invention comprise one or more metal-organic groups, each of which include two or more metal atoms. The metal-organic groups typically function as templates that hold two or more double bond containing organic groups in the proper special orientation to allow cyclization to occur. Typically, the double bonds should be aligned within about 3.2 to about 4.5 Angstroms to facilitate cyclization. In one particular embodiment, the double bonds are aligned within less than about 4.2 Angstroms of each other.

The nature of the metal-organic group is not critical provided it allows the desired special orientation of the double bonds in the associated organic groups. In certain embodiments of the invention, the metal-organic group can be associated with the optical properties (e.g. the fluorescence) of the complexes of the invention, however, this is not a requirement. In one specific embodiment of the invention the metal-organic group is associated with the optical properties (e.g. the fluorescence) of the complexes.

In one embodiment, the metal-organic group can be a Schiff-base complex, for example, a Schiff-base complex as described in *Coord. Chem. Rev.*, 1995, 139, 17; and *Coord. Chem. Rev.*, 1990, 106, 25.

In another embodiment, the metal-organic group can have following structure:

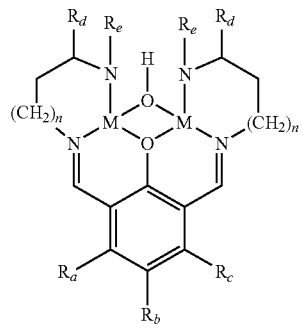

wherein:

each $R_a$, $R_b$, and $R_c$ is independently hydrogen, halo, nitro, cyano, $C_{1-6}$alkyl, $C_{1-6}$alkoxy, $C_{1-6}$alkanoyl, $C_{1-6}$alkanoyloxy, $C_{1-6}$alkoxycarbonyl, trifluoromethyl, (aryl)$C_{1-6}$alkyl, carboxy, or trifluoromethoxy;

each n is independently 0, 1, 2, or 3; and each $R_d$ and $R_e$ is independently hydrogen or $C_{1-6}$alkyl; or $R_d$ and $R_e$ together with the atoms to which they are attached form a 5, 6, 7, or 8 membered saturated or unsaturated ring.

In another embodiment, the metal-organic group can have following structure:

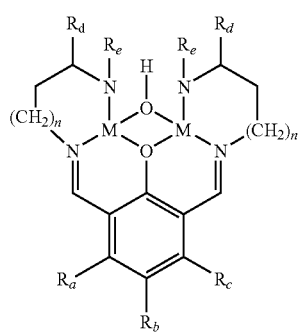

wherein:

each $R_a$, $R_b$, and $R_c$ is independently hydrogen, halo, nitro, cyano, $C_{1-6}$alkyl, $C_{1-6}$alkoxy, $C_{1-6}$alkanoyl, $C_{1-6}$alkanoyloxy, $C_{1-6}$alkoxycarbonyl, trifluoromethyl, or trifluoromethoxy;

each n is independently 0, 1, 2, or 3; and each $R_d$ and $R_e$ is independently hydrogen or $C_{1-6}$alkyl; or $R_d$ and $R_e$ together with the atoms to which they are attached form a 5, 6, 7, or 8 membered saturated or unsaturated ring.

In another specific embodiment of the invention $R_a$ is hydrogen.

In another specific embodiment of the invention $R_b$ is hydrogen.

In another specific embodiment of the invention $R_b$ is halo, nitro, cyano, $C_{1-6}$alkyl, $C_{1-6}$alkoxy, $C_{1-6}$alkanoyl, $C_{1-6}$alkanoyloxy, $C_{1-6}$alkoxycarbonyl, trifluoromethyl, or trifluoromethoxy.

In one specific embodiment of the invention $R_b$ is halo, $C_{1-6}$alkyl, benzyl, or $C_{1-6}$alkoxy.

In another specific embodiment of the invention $R_b$ is halo, or $C_{1-6}$alkyl.

In another specific embodiment of the invention $R_c$ is hydrogen.

In another specific embodiment of the invention each $R_d$ and $R_e$ is independently hydrogen or $C_{1-6}$alkyl.

In another specific embodiment of the invention $R_d$ and $R_e$ together with the atoms to which they are attached form 5 or 6 membered saturated or unsaturated ring.

In another specific embodiment of the invention $R_d$ and $R_e$ together with the atoms to which they are attached form a pyridine, pyrrole, pyrimidine, pyrazine, pyridazine, imidazole, pyrazole, pyrrolidine, piperidine, morpholine, piperazine, or azepine ring.

In another specific embodiment of the invention $R_d$ and $R_e$ together with the atoms to which they are attached form a pyridine, pyrrole, imidazole, pyrrolidine, piperidine, or azepine ring.

In another specific embodiment of the invention $R_d$ and $R_e$ together with the atoms to which they are attached form a pyridine ring.

In another specific embodiment of the invention one or more of the groups MAM has the following structure:

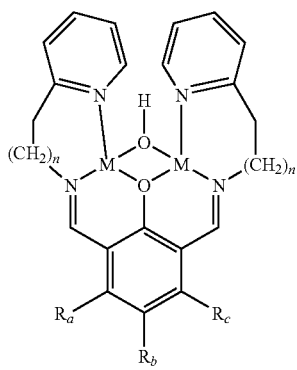

In another specific embodiment of the invention each n is 1.

In another specific embodiment of the invention each ---- designates association by coordination or by a covalent bond.

In another specific embodiment of the invention each $R^1$ independently has the formula X—Y—X; wherein each X is independently hydrogen or a group that is capable of associating with a metal atom; and each Y is independently an organic group comprising one or more double bonds.

In another specific embodiment of the invention each X is independently a group that is capable of associating with a metal atom.

In another specific embodiment of the invention each X independently comprises an amino nitrogen, a thiol, an alcohol, or a carboxylic acid.

In another specific embodiment of the invention each X is independently a 2-pyridyl, 3-pyridyl, or 4-pyridyl ring.

In another specific embodiment of the invention each X is a 4-pyridyl ring.

In another specific embodiment of the invention each Y has 1-10 double bonds.

In another specific embodiment of the invention each Y has 1-5 double bonds.

In another specific embodiment of the invention each Y has one double bond.

Depending on the structure of the metal-organic group and other associated groups, the complexes of the invention may optionally comprise one or more counter ions and be charged. The charge of the complex may also be neutral.

Association Between Metal-Organic Groups and Organic Groups

The double bond containing organic groups can be "associated" with the metal-organic templates by any suitable attractive force, such as, for example, ionic bonds, covalent bonds, or non-covalent bonds (e.g. dipole-dipole interactions, hydrogen bonds, van der Waals interactions, or coordination).

Organic Group

The nature of the organic groups is not critical provided they have one or more double bonds capable of reacting as described herein. In one embodiment, the organic groups comprise about 1-20 double bonds. In another embodiment, the organic groups comprises 1-12 double bonds. In another embodiment, the organic groups comprises 1-10 double bonds. In yet another embodiment, the organic groups comprises 1-6 double bonds. In another embodiment, the organic groups comprises 1-5 double bonds. In another embodiment, the organic groups comprises 1 double bond. In yet another embodiment, the organic groups comprise only trans double bonds. In yet another embodiment, the organic groups comprise only cis double bonds. In yet another embodiment, the organic groups comprise a mixture of cis and trans double bonds. The organic groups can be branched or unbranched and they can include other functionality such as aryl and heteroaryl rings, heteroatoms and substituents, provided the other functionality does not interfere with the association of the polyenes with the templates. In one embodiment of the invention the organic groups can comprise one or more fluorescent groups. Typically the organic groups comprises from about 2 to about 40 carbon atoms. In one embodiment, the organic groups comprises from about 2 to about 30 carbon atoms. In another embodiment the organic groups comprises from about 2 to about 20 carbon atoms.

In one embodiment of the invention, each organic group is substituted with a group or groups that are capable of associating with the metal-organic template. For example, each organic group can independently comprise an amino nitrogen, a thiol, an alcohol, or a carboxylic acid. In one embodiment each organic group is substituted with a group or groups that are capable of forming a coordination bond with the metal. In another embodiment, each organic group is substituted with a pyridine ring (e.g. a 2-pyridyl, 3-pyridyl, or 4-pyridyl ring).

In another embodiment of the invention, each organic group is terminally substituted with a group or groups that are capable of associating with the metal-organic template. For example, each organic group can independently comprise an amino nitrogen, a thiol, an alcohol, or a carboxylic acid. In one embodiment each organic group is terminally substituted with a group or groups that are capable of forming a coordination bond with the metal. In another embodiment, each organic group is terminally substituted with a pyridine ring (e.g. a 2-pyridyl, 3-pyridyl, or 4-pyridyl ring).

Cyclization Reactions

The reaction of the double bonds to form the cyclobutane rings can be carried out under any suitable conditions. Typically, the reaction is carried out in a solid state (e.g. a crystalline state). The reaction can be initiated using any suitable means. For example, the reaction can conveniently be initiated with an energy source, such as heat, electric current, or light (e.g. UV light).

Metal Atoms

The term "metal atom" includes all known metals in any oxidation state, provided the metal atom can associate with an organic group and participate in orienting the organic group for reaction as described herein. For example, reference to a metal atom being Zn includes all oxidation states of Zn, unless a specific oxidation state (e.g. $Zn^{2+}$) is specifically designated.

As used herein, "transition metal" includes the elements located between columns IIA and IIIA in the periodic table. For example, the term "transition metal" includes Scandium, Titanium, Vanadium, Chromium, Manganese, Iron, Cobalt, Nickel, Copper, Zinc, Yttrium, Zirconium, Niobium, Molybdenum, Technetium, Ruthenium, Rhodium, Palladium, Silver, Cadmium, Hafnium, Tantalum, Tungsten, Rhenium, Osmium, Iridium, Platinum, Gold, Mercury, Rutherfordium, Dubnium, Seaborgium, Bohrium, Hassium, Meitnerium, Ununnilium, Unununium, and Ununbium.

In one specific embodiment of the invention each metal atom is independently Sc, Ti, V, Cr, Mn, Fe, Co, Ni, Cu, Zn, Y, Zr, Nb, Mo, Tc, Ru, Rh, Pd, Ag, Cd, La, Hf, Ta, W, Re, Os, Ir, Pt, Au, or Hg.

In another specific embodiment of the invention each metal atom is independently Sc, Ti, V, Cr, Mn, Fe, Co, Ni, Cu, or Zn.

In another specific embodiment of the invention each metal atom is independently Y, Zr, Nb, Mo, Tc, Ru, Rh, Pd, Ag, or Cd.

In another specific embodiment of the invention each metal atom is independently La, Hf, Ta, W, Re, Os, Ir, Pt, Au, or Hg.

In another specific embodiment of the invention each metal atom is Fe, Co, or Ni.

In another specific embodiment of the invention each metal atom is Zn (e.g. Zn, $Zn^{1+}$, or $Zn^{2+}$)

Methods of the Invention

In one specific embodiment the invention provides a method comprising: forming a complex of the invention on a substrate and irradiating the complex to form a material having a characteristic fluorescent energy.

In one specific embodiment the invention provides a method comprising: forming a complex of the invention on a substrate; irradiating the complex to form a material having a characteristic fluorescent energy; irradiating the material; and detecting the characteristic fluorescent energy.

In one specific embodiment the invention provides a method comprising: forming a complex of the invention on a substrate and passing a current through the complex to form a material having a characteristic fluorescent energy.

In one specific embodiment the invention provides a method comprising: forming a film of a complex of the invention on a substrate; and irradiating the complex to form a material having a plurality of characteristic fluorescent energies.

In one specific embodiment the invention provides a method comprising: forming a film of a complex of the invention on a substrate; irradiating the complex to form a material having a plurality of characteristic fluorescent energies; and irradiating the material to produce at least one of the plurality of characteristic fluorescent energies.

In one specific embodiment the invention provides a method comprising: forming a film of a complex of the invention on a substrate; irradiating the complex to form a material having a plurality of characteristic fluorescent energies; and irradiating the material to produce at least one of the plurality of characteristic fluorescent energies.

In one specific embodiment the invention provides a method comprising: forming a film of a complex of the invention on a substrate; irradiating the complex to form a material having a plurality of characteristic fluorescent energies; and irradiating the material using a plurality of radiation sources to produce at least one of the plurality of characteristic fluorescent energies.

In one specific embodiment the invention provides a method comprising: forming a film of a complex of the invention on a substrate; irradiating the complex to form a material having a plurality of characteristic fluorescent energies by forming radiated and non-radiated areas in the film; and irradiating the material to produce at least one of the plurality of characteristic fluorescent energies.

Apparatuses of the Invention

In one specific embodiment the invention provides an apparatus comprising: a substrate; and a complex of the invention formed on the substrate.

In one specific embodiment the substrate comprises silicon.

In another specific embodiment the substrate comprises gallium arsenide.

In another specific embodiment the substrate comprises an amorphous material.

In another specific embodiment the amorphous material comprises a glass.

In one specific embodiment the invention provides an apparatus comprising: a first translucent material; a second translucent material; and a film including a complex of the invention formed between the first translucent material and the second translucent material.

In one specific embodiment the invention provides an apparatus comprising: a first translucent material; a second translucent material; a film including a complex of the invention formed between the first translucent material and the second translucent material; a radiation source optically coupled to the film through the first translucent material; and a radiation detector optically coupled to the film through the second translucent material.

In one specific embodiment the invention provides an apparatus comprising: a first translucent material; a second translucent material; and a film including a complex of the invention formed between the first translucent material and the second translucent material, wherein the complex fluoresces at a fluorescent energy and the second material is substantially translucent at the fluorescent energy.

In one specific embodiment the invention provides an apparatus comprising: a radiation source; a complex of the invention to receive radiation from the radiation source; and a radiation detector to detect radiation emitted from the complex.

In one specific embodiment the invention provides an apparatus comprising: a radiation source; a complex of the invention to receive radiation from the radiation source; and a radiation detector to detect radiation emitted from the complex, wherein the radiation source emits radiation at about 290 nanometers.

In one specific embodiment the invention provides an apparatus comprising: a radiation source; a complex of the invention to receive radiation from the radiation source; and a radiation detector to detect radiation emitted from the complex, wherein the radiation detector detects radiation at about 520 nanometers.

In one specific embodiment the invention provides an apparatus comprising: a substrate; a first complex of the invention formed on the substrate, the complex tuned to fluoresce at a first energy; and a second complex of the invention formed on the first complex, the second complex tuned to fluoresce at a second energy, the second energy being different from the first energy.

In one specific embodiment the invention provides an apparatus comprising: a substrate; a first complex of the invention formed on the substrate, the complex tuned to fluoresce at a first energy; and a second complex of the invention formed on the first complex, the second complex tuned to fluoresce at a second energy, the second energy being different from the first energy, wherein the substrate comprises a semiconductor.

In one specific embodiment the invention provides an apparatus comprising: a substrate; a first complex of the invention formed on the substrate, the complex tuned to fluoresce at a first energy; and a second complex of the invention formed on the first complex, the second complex tuned to fluoresce at a second energy, the second energy being different from the first energy, wherein the substrate comprises a semiconductor and wherein the substrate comprises gallium arsenide.

In one specific embodiment the invention provides an apparatus comprising: a substrate; a first complex of the invention formed on the substrate, the complex tuned to fluoresce at a first energy; and a second complex of the invention formed on the first complex, the second complex tuned to fluoresce at a second energy, the second energy being different from the first energy, wherein the substrate comprises a semiconductor, and wherein the substrate comprises silicon.

In one specific embodiment the invention provides a system comprising: a processor; a radiation source coupled to the processor; a complex of the invention formed on a substrate to receive radiation from the radiation source; and a radiation detector coupled to the processor, the radiation detector to detect radiation emitted from the complex.

In one specific embodiment the invention provides a system comprising: a processor; a radiation source coupled to the processor; a complex of the invention formed on a substrate to receive radiation from the radiation source; and a radiation detector coupled to the processor, the radiation detector to detect radiation emitted from the complex, wherein the processor comprises a reduced instruction set processor.

In one specific embodiment the invention provides a system comprising: a processor; a radiation source coupled to the processor; a complex of the invention formed on a substrate to receive radiation from the radiation source; and a radiation detector coupled to the processor, the radiation detector to detect radiation emitted from the complex, wherein the radiation source comprises an ultraviolet radiation source.

In one specific embodiment the invention provides a system comprising: a processor; a radiation source coupled to the processor; a complex of the invention formed on a substrate to receive radiation from the radiation source; and a radiation detector coupled to the processor, the radiation detector to detect radiation emitted from the complex, wherein the radiation detector comprises a ultraviolet radiation detector.

Figures

FIG. 1 is a perspective view of an apparatus 100 including a substrate 102 and a complex of the invention 104 formed on the substrate 102 in accordance with some embodiments of the invention. The substrate 102 is a base upon which the complex of the invention 104 is formed. The substrate 102 is not limited to a particular material or a material having a particular flexibility. Exemplary crystalline materials suitable for use in the fabrication of the substrate 102 include semiconductors, such as silicon, germanium, and gallium arsenide. Exemplary amorphous materials suitable for use in the fabrication of the substrate 102 include glass and amorphous silicon. Substantially rigid substrates, such as substrates formed from single crystal semiconductors, such as, for example germanium, are suitable for use in connection with the fabrication of the substrate 102 of the apparatus 100. Alternatively, flexible substrates, such as substrates formed from polyester films, are also suitable for use in connection with the fabrication of the substrate 102 of the apparatus 100. The complex of the invention 104 is not limited to a particular complex of the invention. Complexes in which the material includes a tunable fluorescence are suitable for use in connection with the fabrication of the apparatus 100. Exemplary complexes are described herein.

FIG. 2A is a perspective view of an apparatus 200 including a first translucent material 202, a second translucent material 204, and a film 206 including a complex of the invention formed between the first translucent material 202 and the second translucent material 204 in accordance with some embodiments of the invention. The first translucent material 202 includes a surface 208. The second translucent material 204 includes an surface 210. A translucent material is a material that allows transmission of radiation. The first translucent material 202 and the second translucent material 204 allow the transmission of radiation. However, the radiation transfer function of the first translucent material 202 and the radiation transfer function of the second translucent material 204 are not limited to being substantially the same. For example, the first translucent material 202 can be selected to transmit energy at about 500 nanometers, and the second translucent material 204 can be selected to transmit energy at about 300 nanometers. A film is a thin coating. A monolayer is about one molecule thick. A thin coating includes coatings having a thickness of between about a monolayer and about several thousand monolayers. The film 206 includes a complex of the invention, such as a material having a tunable fluorescence, and coats surface 208 of the first translucent material 202 and the surface 210 of the second translucent material 204.

Figure 2B:
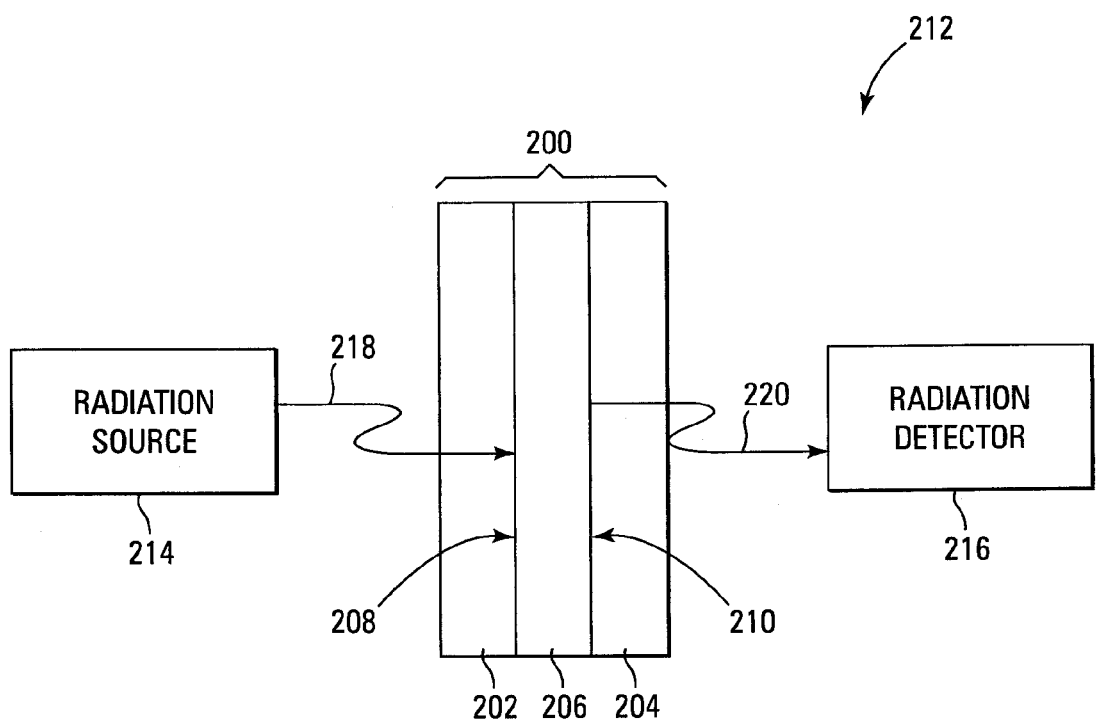
FIG. 2B is a block diagram of an apparatus including the apparatus, shown in FIG. 2A, a radiation source, and a radiation detector in accordance with some embodiments of the invention.

FIG. 2B is a block diagram of an apparatus 212 including the apparatus 200, shown in FIG. 2A, a radiation source 214, and a radiation detector 216 in accordance with some embodiments of the invention. The apparatus 200 includes the first translucent material 202, the second translucent material 204, and the film 206 including a complex of the invention formed between the first translucent material 202 and the second translucent material 204. The first translucent material 202 includes a surface 208. The second translucent material 204 includes an surface 210. The radiation source 214 is optically coupled to the film 206 through the first translucent material 202. The radiation detector 216 is optically coupled to the film 206 through the second translucent material 204. In some embodiments, the complex of the invention 206 fluoresces at a fluorescent energy and the second translucent material 204 is substantially translucent at the fluorescent energy of the complex of the invention 206. The radiation source 214 is not limited to a particular type of radiation source. Exemplary radiation sources suitable for use in the fabrication of the apparatus 212 include an ultraviolet radiation source and a laser radiation source tuned to one or more wavelengths in the ultraviolet region of the electromagnetic spectrum. The radiation detector 216 is not limited to a particular type of radiation detector. Exemplary radiation detectors suitable for use in connection with the fabrication of the apparatus 212 include photomultiplier tubes and semiconductor detectors. Exemplary semiconductor detectors suitable for use in connection with the fabrication of the apparatus 212 include detectors fabricated from silicon, germanium, or gallium arsenide. In operation, the radiation source 214 emits radiation 218 that stimulates the emission of radiation 220 through fluorescence of the complex of the invention included in the film 206. The radiation 220 is detected at the radiation detector 216.

Figure 3:
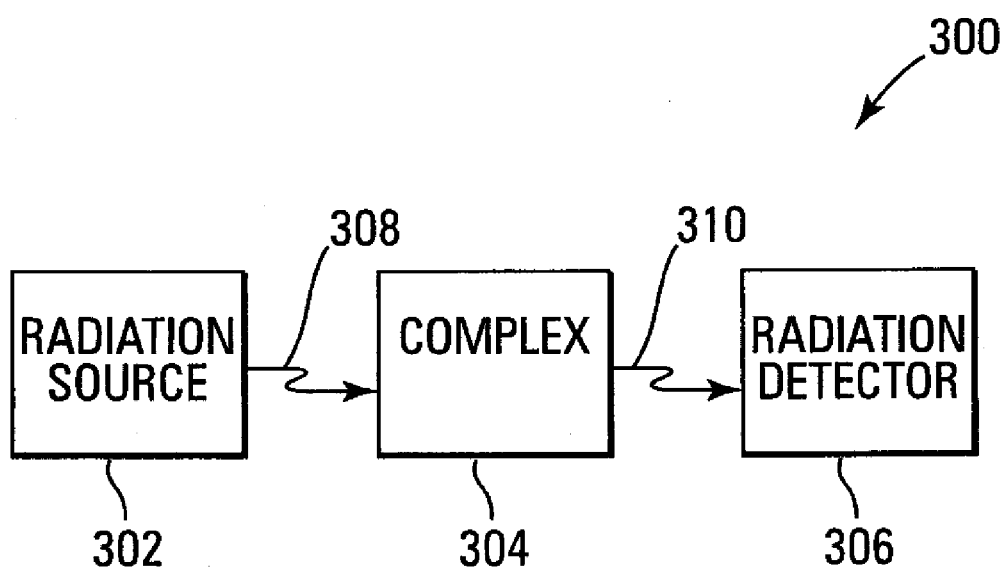
FIG. 3 is a block diagram of an apparatus including a radiation source, a complex of the invention, and a radiation detector in accordance with some embodiments of the invention.

FIG. 3 is a block diagram of an apparatus 300 including a radiation source 302, a complex of the invention 304, and a radiation detector 306 in accordance with some embodiments of the invention. In operation, the radiation source 302 emits radiation 308. The complex of the invention 304 receives the radiation 308 from the radiation source 302. In some embodiments, the radiation source emits radiation at about 290 nanometers. The complex of the invention 304 emits radiation 310. In some embodiments, the complex of the invention 304 emits radiation at about 520 nanometers. The radiation 310 is emitted from the complex of the invention 304 after receiving the radiation 308 from the radiation source 302. The radiation detector 306 detects radiation emitted from the complex of the invention 304.

Figure 4:
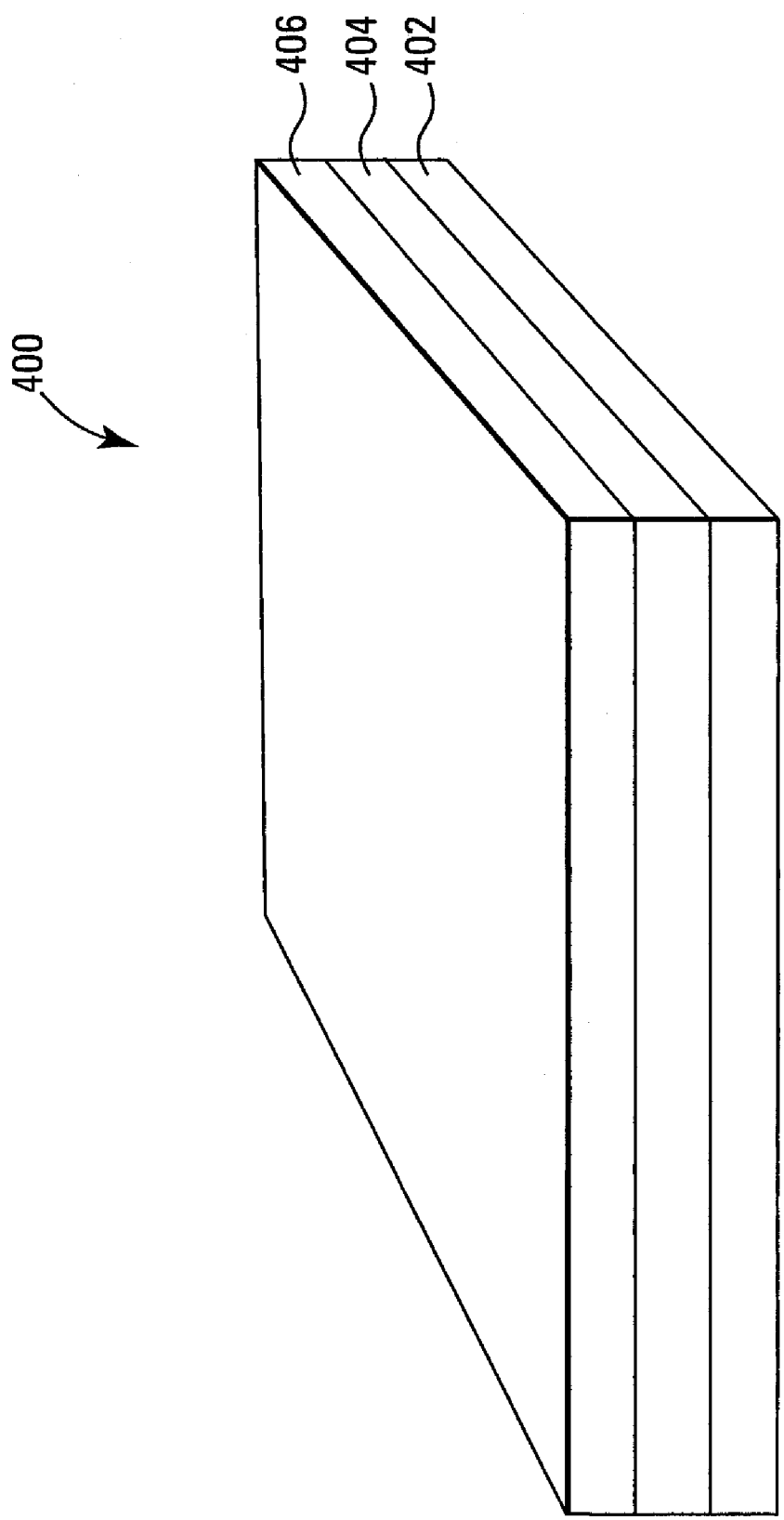
FIG. 4 is a perspective view of an apparatus including a substrate, a first complex of the invention formed on the substrate, and a second complex of the invention formed on the first complex of the invention in accordance with some embodiments of the invention.

FIG. 4 is a perspective view of an apparatus 400 including a substrate 402, a first complex of the invention 404 formed on the substrate 402, and a second complex of the invention 406 formed on the first complex of the invention 404 in accordance with some embodiments of the invention. Exemplary substrate materials suitable for use in the fabrication of the apparatus 400 include semiconductors, such as silicon, germanium, and gallium arsenide. In some embodiments, the first complex of the invention 404 is tuned to exhibit fluorescence at a first energy and the second complex of the invention 406 is tuned to exhibit fluorescence at a second energy with the second energy being different from the first energy. Stacking the first complex of the invention 404 and the second complex of the invention 406 permits the storing of information in three dimensions in the apparatus 400.

Figure 5:
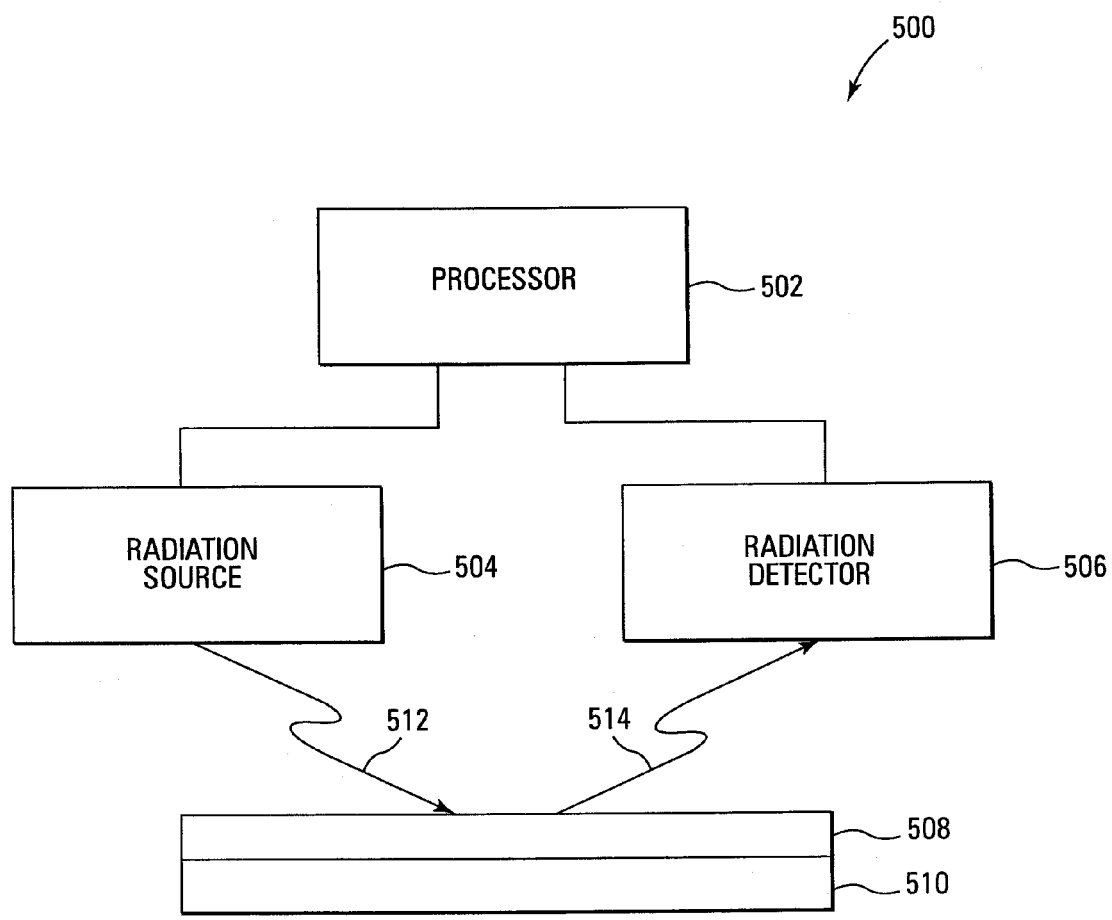
FIG. 5 is a block diagram of a system including a processor, a radiation source, a radiation detector, and a complex of the invention formed on a substrate in accordance with some embodiments of the invention.

FIG. 5 is a block diagram of a system 500 including a processor 502, a radiation source 504, a radiation detector 506, and a complex of the invention 508 formed on a substrate 510 in accordance with some embodiments of the invention. The processor is coupled to the radiation source 504 and the radiation detector 506. The processor 502 is not limited to a particular type of processor. Exemplary processors suitable for use in the fabrication of the system 500 include reduced instruction set processors, complex instruction set processors, very long word instruction word processors, and digital signal processors. In some embodiments, the radiation source 504 includes an ultraviolet radiation source. In some embodiments, the radiation detector 506 includes an ultraviolet radiation detector, such as a semiconductor detector. The complex of the invention 508 includes materials exhibiting photo-fluorescence, such as those described herein. The substrate 510 includes materials suitable for acting as a base for the complex of the invention 508. Exemplary substrate materials include semiconductors, amorphous materials, such as glass and amorphous semiconductors, and polyester films. In operation, the processor 502 provides information to control the emission of radiation 512 by the radiation source 504. In some embodiments, the processor 502 controls the wavelength of the radiation 512 and the duration of the radiation 512. The detector receives radiation 514 from the complex of the invention 508 and provides information related to the wavelength of the radiation 514 to the processor 502.

Figure 6:
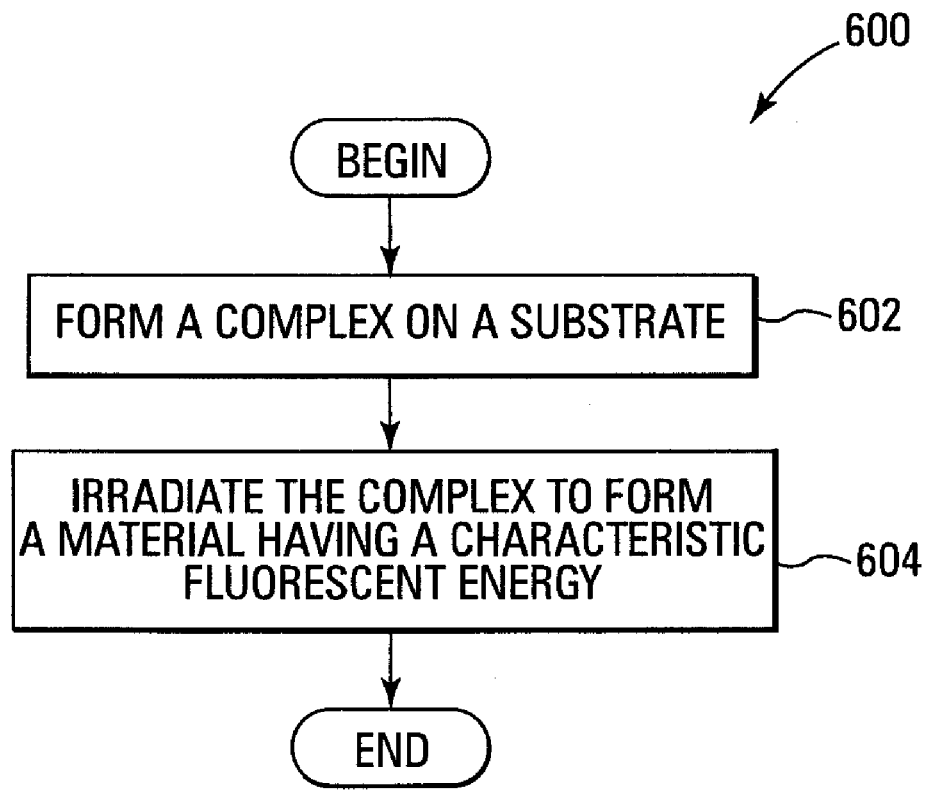
FIG. 6 is a flow diagram of a method including forming a complex of the invention on a substrate and irradiating the complex of the invention to form a material having a characteristic fluorescent energy in accordance with some embodiments of the invention.

FIG. 6 is a flow diagram of a method 600 including forming a complex of the invention on a substrate (block 602) and irradiating the complex of the invention to form a material having a characteristic fluorescent energy (block 604) in accordance with some embodiments of the invention. In some embodiments, the method 600 further includes irradiating the complex of the invention and detecting the characteristic fluorescent energy. In some embodiments, irradiating the complex of the invention includes irradiating the complex of the invention at about 290 nanometers. In some embodiments, the method 600 includes irradiating the material to transform the material into the complex of the invention. In some embodiments, irradiating the complex of the invention to form a material having a characteristic fluorescent energy includes irradiating the complex of the invention with an mercury source. In some embodiments, irradiating the complex of the invention to form a material having a characteristic fluorescent energy includes irradiating the complex of the invention at about 419 nanometers. In some embodiments, the method 600 further includes passing a current through the material, and detecting the characteristic fluorescence energy.

Figure 7:
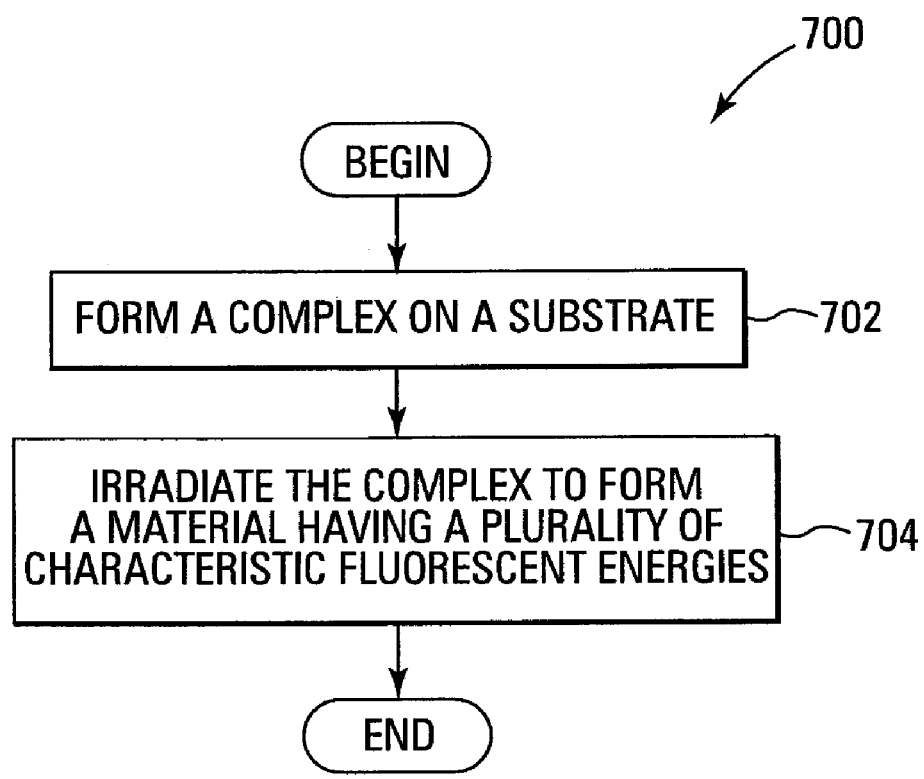
FIG. 7 is a flow diagram of a method including forming a complex of the invention on a substrate and irradiating the complex of the invention to form a material having a plurality of characteristic fluorescent energies in accordance with some embodiments of the invention.

FIG. 7 is a flow diagram of a method 700 including forming a complex of the invention on a substrate (block 702) and irradiating the complex of the invention to form a material having a plurality of characteristic fluorescent energies (block 704) in accordance with some embodiments of the invention. In some embodiments, the method 700 includes irradiating the material to produce at least one of the plurality of characteristic fluorescent energies. In some embodiments, irradiating the complex of the invention to form the material having the plurality of characteristic fluorescent energies includes irradiating the complex of the invention using a plurality of radiation sources. In some embodiments, irradiating the complex of the invention to form a material having a plurality of characteristic fluorescent energies includes forming radiated and non-radiated areas in the film.

The invention will now be illustrated by the following non-limiting Examples. In Examples 1 and 2 coordination-driven self-assembly was used to direct a photoinduced [2+2] cyclodimerization in the solid state. Specifically, a dinuclear Zn complex was used to assemble 4,4'-bpe [where: 4,4'-bpe=trans-1,2-bis(4-pyridyl)ethylene)] within a representative tetranuclear rectangular complex of the invention.

EXAMPLES

Example 1

Preparation of Representative Complex of the Invention (Complex 1)

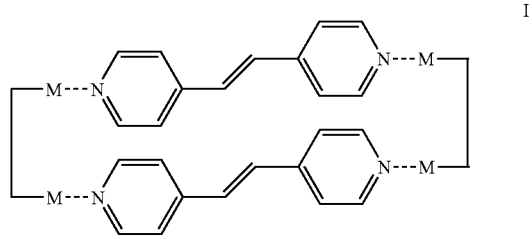

I

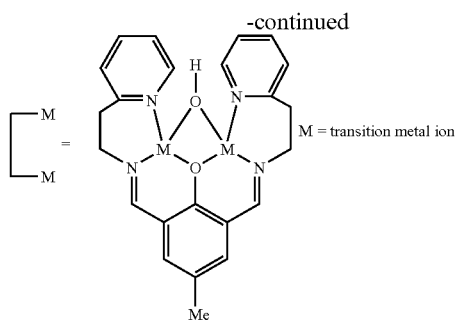

-continued

M = transition metal ion

Ditopic LH was synthesized from condensation of 2-hydroxy-5-methyl-isophthalaldehyde (0.84 g) with 2-aminoethyl-pyridine (1.24 g) (1:2 ratio) in MeOH (15 mL) (Visinescu, D. et al., *Inorg. Chem. Commun.* 2002, 5, 42). Dissolution of $Zn(ClO_4)_2.6H_2O$ (0.37 g) and $LiOH.H_2O$ (0.03 g) in $H_2O$ (5 mL) (2:3 ratio) produced a yellow solution. Diffusion of a MeOH solution (10 mL) of 4,4'-bpe (0.90 g) into the aqueous Zn(II) and Li(I) solution (ratio: 4:2:3) resulted in precipitation of a light-yellow crystals of $[Zn_4L_2(OH)_2(4,4'\text{-bpe})_2](ClO_4)_4.4H_2O$ 1 (where: LH=2,6-bis[N-(2-pyridylethyl)formimidoyl]-4-methylphenol) over a period of two weeks (yield: 76%), as illustrated below.

Figure 8A:
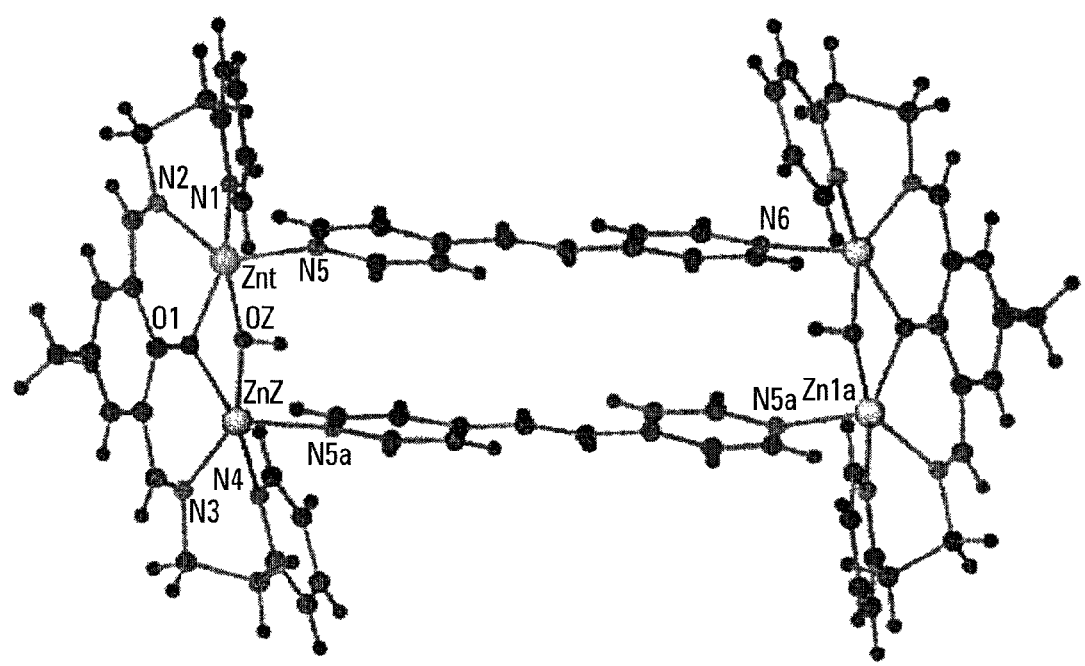
FIG. 8 X-ray crystal structure of complex 1 prepared in Example 1: ball-and-stick views of (a) tetranuclear assembly and (b) hydrogen-bonded array. Color scheme: Zn=yellow, Cl=gray; C=blue; O=red; N=green; C=blue; H=black.
Figure 8B:
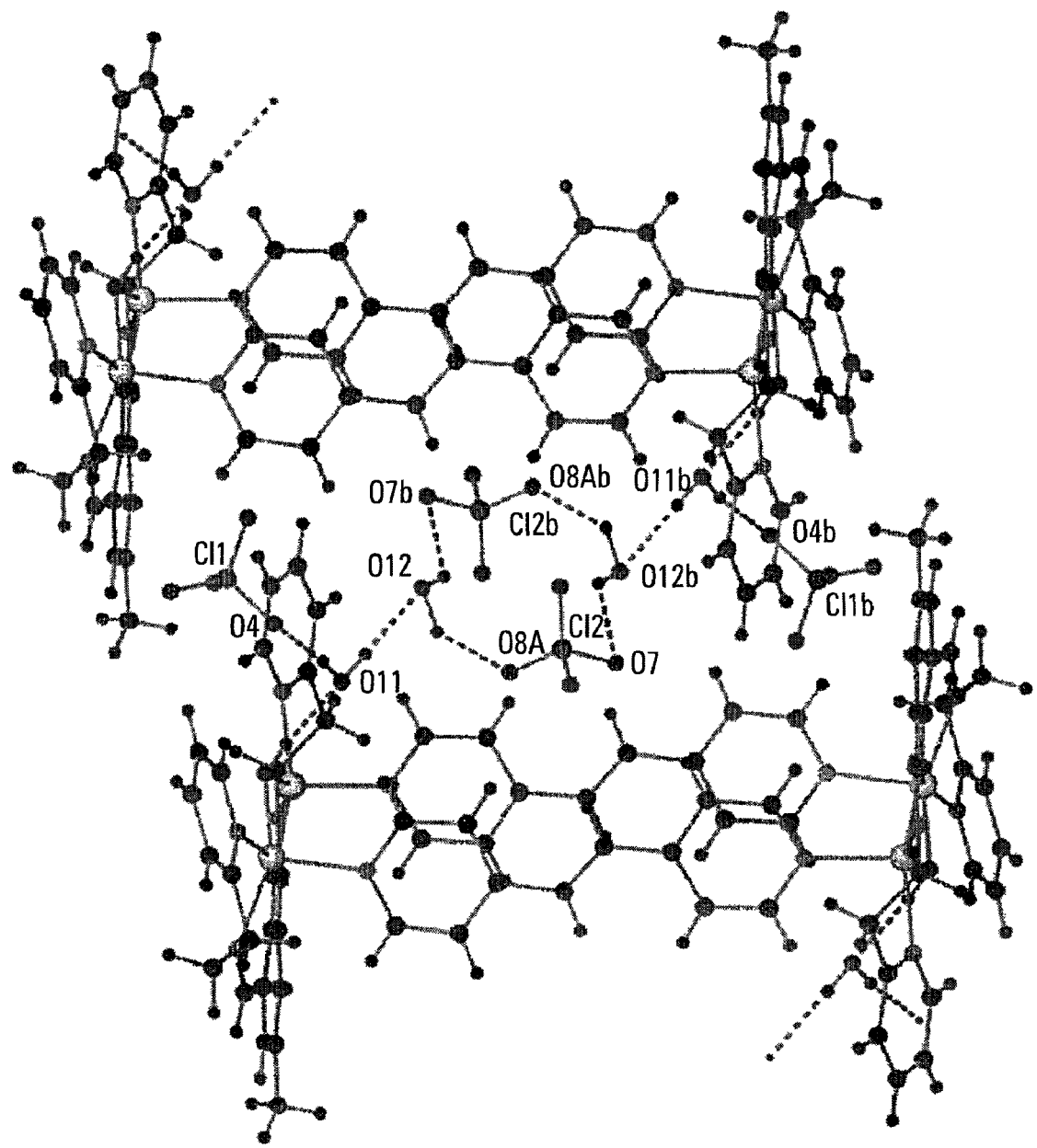

A view of the crystal structure of 1 (FIG. 8; X-ray data for 1: triclinic, space group P$\bar{1}$, α=10.7509(11), b=10.9233(11), c=18.558(2), α=97.531(5) β=101.758(5)°, γ=110.933(5)°, U=1942.7(4)Å$^3$ for Z=1 and R=0.046) reveals that two dinuclear $[Zn_2L(OH)]^{2+}$ units assemble with two molecules of 4,4'-bpe to form a tetranuclear rectangular assembly, $[Zn_4L_2(OH)_2(4,4'\text{-bpe})_2]^{4+}$, sustained by four Zn—N bonds [Zn—N (Å): Zn(1)-N(5) 2.090(3), Zn(2)-N(6)a 2.105(3) (a: −x+1, −y+2, −z+2)] (FIG. 8a). Each metal [Zn . . . Zn (Å): Zn(1)-Zn(2) 3.135(1), Zn(1)-Zn(2)a 13.542] adopts a square pyramidal geometry where the pyridyl N— atoms of 4,4'-bpe occupy the apical positions while the remaining sites are occupied by a single O- and two N-atoms of L and a single O-atom of a $\mu_2$-OH$^-$ ion. Each assembly is surrounded by two $ClO_4^-$ ions, one which lies disordered across two sites A and B (occupancies: (A) 0.53, (B) 0.47), and two water molecules that assemble with the OH$^-$ ligand to form a 1D hydrogen-bonded array with cavities filled by four $ClO_4^-$ ions and four water molecules [O . . . O (Å): O(2) . . . O(11) 2.888(5), O(11) . . . O(12) 2.804(6), O(11) . . . O(4) 2.787(5), O(12) . . . O(8A) 3.03(1), O(12) . . . O(7)b 3.063(8), (b: −x+1, −y+1, −z+2)] (FIG. 8b). In this arrangement, the C═C bonds of the assembly lie parallel and separated by 3.64 Å. This geometry conforms to the topochemical postulate of Schmidt for [2+2] photoreaction (Schmidt, G. M. J. *Pure Appl. Chem.* 1971, 27, 647). C═C bonds of nearest-neighbor assemblies lie offset and separated by 9.82 Å such that the C═C bonds of the polygonal assembly are the sole olefins organized for reaction.

Example 2

Preparation of Representative Complex of the Invention (Complex 2)

Exposure of either single crystals or a powdered crystalline sample of complex 1 to UV radiation, using either a broad-band or a 419 nm Hg lamp (Enkelmann, V. et al., *J. Amer. Chem. Soc.* 1993, 115, 10390), for a period of 5 hours resulted in dimerization of 4,4'-bpe to give rctt-tetrakis(4-pyridyl)cyclobutane (4,4'-tpcb) complex 2 in 100% yield as illustrated below.

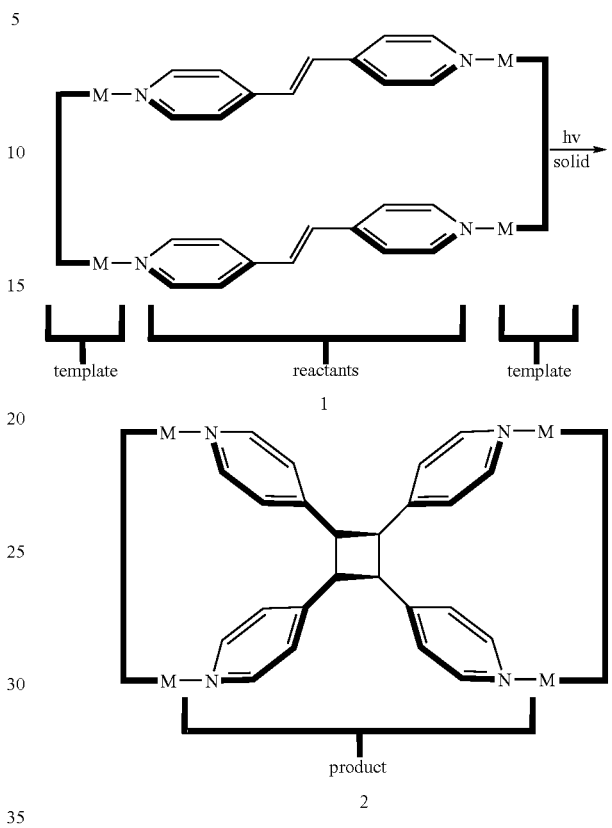

The reaction occurs via a single-crystal-to-single-crystal (SCSC) transformation (Enkelmann, V. et al, *Amer. Chem. Soc.* 1993, 115, 10390) that exhibits a red shift in fluorescence (Tyson, D. S. et al., *J. Am. Chem. Soc.* 2002, 124, 4562; Pistolis, G. et al., *Chem. Mater.* 2002, 14, 790) from blue to green.

The identity of 4,4'-tpcb in 2 was confirmed by $^1$H NMR spectroscopy. Optical microscopy revealed the transparency and shape of the single crystals exposed to the 419 nm UV source (Enkelmann, V. et al., *J. Amer. Chem. Soc.* 1993, 115, 10390) remained intact during the photoreaction, which suggested the reaction occurred via a SCSC transformation.

Figure 9A:
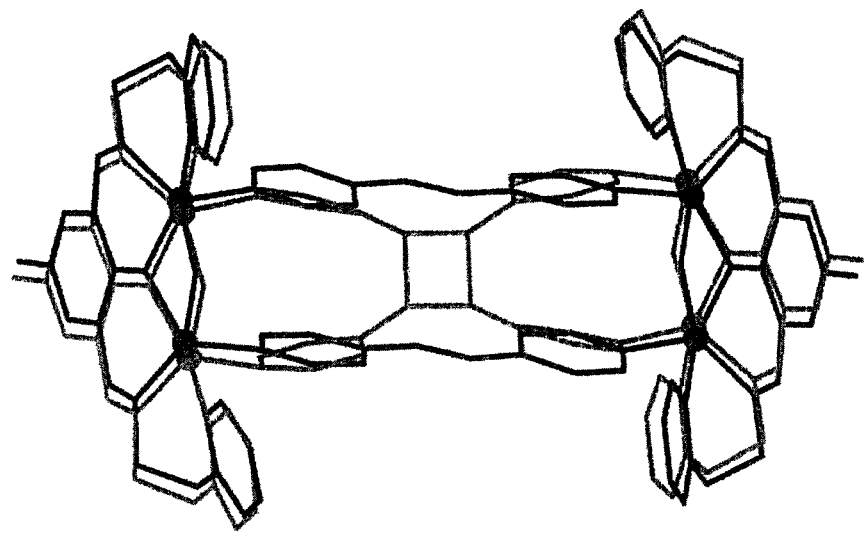
FIG. 9. Overlay views of complex 1 (blue) and complex 2 formed in Example 2 (green): (a) tetranuclear assembly and (b) hydrogen-bonded array.
Figure 9B:
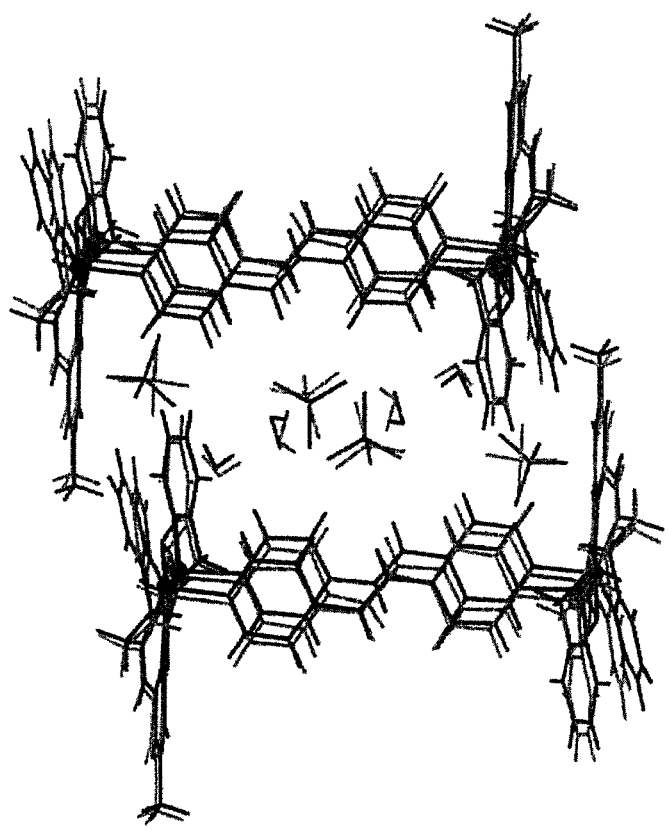

A single-crystal X-ray diffraction analysis of photoreacted 1 (X-ray data for 2: triclinic, space group P$\bar{1}$, a=10.9644(11), b=11.2922(11), c=17.6367(18), α=96.933(5)°, β=101.342(5)°, γ=113.218(5)°, U=1919.4(3)Å3 for Z=1 and R=0.044) confirmed the solid-state reaction occurred via a SCSC transformation (FIG. 9). Overlay views of 1 and 2 reveal that the olefins dimerized to give 4,4'-tpcb (FIG. 9a). In this arrangement, 4,4'-tpcb lies within 2 such that the pyridyl groups, which adopt a unsymmetrical boat conformation and lie inclined by approximately 120 with respect to the basal planes of the metals, interact with the Schiff-base complex within a tetranuclear assembly, similar to 1, sustained by four Zn—N bonds (Zn—N (Å): Zn(1)-N(5) 2.094(3), Zn(2)-N(6) 2.106(3). To accommodate 4,4'-tpcb, the distances between the metals within and between the Schiff-base ligands have slightly increased and decreased, respectively [Zn . . . Zn (A): Zn(1)-Zn(2) 3.182(1), Zn(1)-Zn(2)c 13.36 (c: −x+1, −y+1, −z+1)], while the hydrogen-bonded array has undergone a slight deformation, the most significant being a 1.15 Å displacement of the ordered $ClO_4^-$ ion toward the center of each inclusion cavity (FIG. 9b).

Example 3

Fluorescence of Complex 1 and Complex 2

Figure 10A:
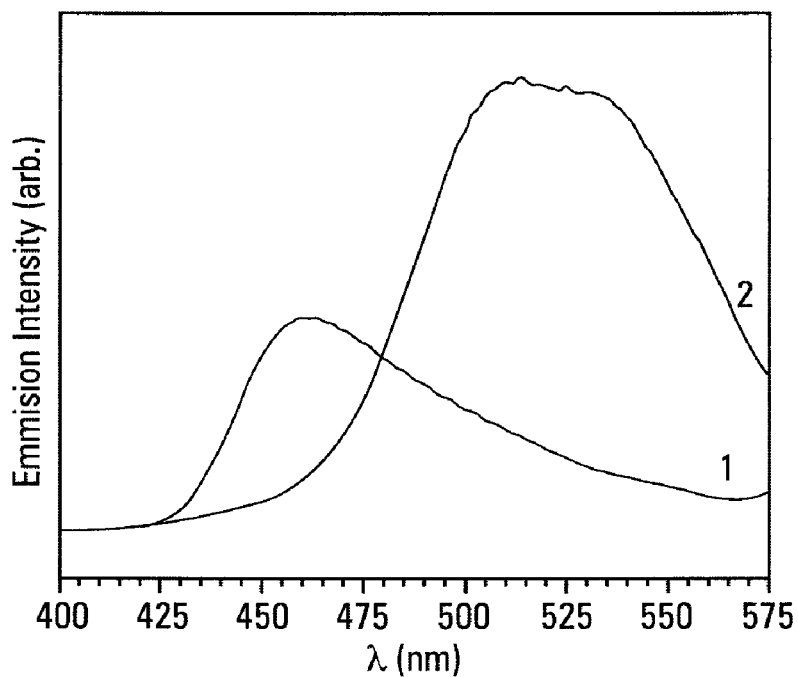
FIG. 10. Spectra of complex 1 and complex 2: (a) emission spectra (290 nm excitation) (inset: microscope images of fluorescence of single crystals of complex 1 and complex 2 at 40× magnification) and (b) confocal fluorescence microscopy data comparing ratios of intensities at 510 nm and 480 nm (blue=complex 1; green=complex 2). Each ratio image taken for a 10 μm×30 μm cross section ~12 μm from crystal surface. Cross section is ~1 μm thick. Spatial resolutions: 50 nm in xy-plane and ~1 μm along z-axis.
Figure 10B:
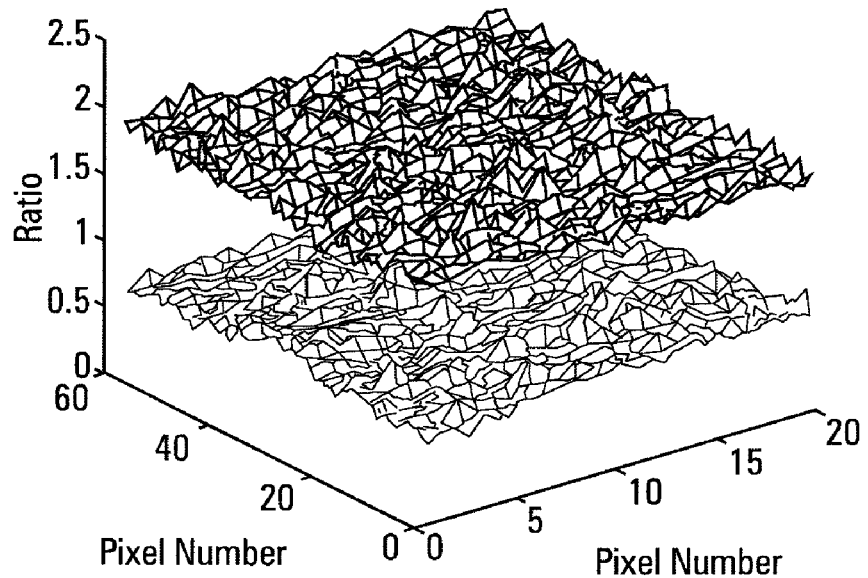

Illumination of complex 1 and complex 2 at room temperature with UV energy reveals that complex 2 exhibits a remarkably different fluorescence emission than complex 1 (FIG. 10). Specifically, excitation of complex 1 at 290 nm gives blue emission at 464 nm while similar excitation of complex 2 gives green emission at 520 nm (FIG. 10a). Illumination of cleaved crystals of complex 1 and complex 2 using a handheld UV lamp demonstrates that the emissions are propagated from the bulk, an observation confirmed by laser scanning confocal fluorescence microscopy which reveals a consistent difference in fluorescence between complex 1 and complex 2, as determined by comparing ratios of the fluorescence at 480 nm and 510 nm (FIG. 10b), at different depths in each single-crystalline solid.

Example 4

Preparation of Representative Complex of the Invention (Complex 3)

During experiments to generalize complex 1 as a template to direct the [2+2] photodimerisation in the solid state, it was discovered that 1 could assemble with 4,4'-bpe to form an infinite, one-dimensional (1D) ladder-like coordination polymer Complex 3 [(1)(4,4'-bpe)$_2$](ClO$_4$)$_2$.4H$_2$O.

Pale yellow single crystals of Complex 3 were obtained by slow evaporation of an ethanolic solution (25 mL) of [Zn$_2$L(OH)](ClO$_4$)$_2$ (0.32 g, 0.5 mmol) and 4,4'-bpe (0.91 g, 0.5 mmol) (molar ratio: 1:1) over a period of 2 days (yield: 72%). The composition of Complex 3 was confirmed via single-crystal and powder X-ray diffraction data, as well as thermal gravimetric analysis.

A single-crystal X-ray structure analysis of Complex 3 demonstrates that, similar to Complex 1 the metal and organic components have assembled such that the bipyridines are organized, via Zn—N bonds, in a face-to-face stacked arrangement. The two Zn atoms of Complex 3 are separated by 3.19 Å (cf. [Complex 1: 3.14 Å) while the carbon-carbon double (C=C) bonds of the stacked olefins lie parallel and separated by 3.71 Å (cf. Complex 1: parallel, 3.64 Å). The geometry of the stacked olefins conforms to criteria of Schmidt for [2+2] photoreaction in a solid. In contrast to Complex 1, however, each Zn ion of Complex 3 lies in an octahedral, rather than a square-pyramidal, coordination environment such that two N-atoms of two 4-pyridyl groups adopt a transoid arrangement. The remaining coordination sites of each Zn ion are occupied by a single O— and two N-atoms of pentadentate L and a single O-atom of a µ-OH ion.

The transoid arrangement of the 4-pyridyl groups of Complex 3 is propagated in space such that Complex 3 and 4,4'-bpe assemble to form a 1D ladder-like coordination polymer along the crystallographic (101) direction. The pentadentate L units are oriented anti-parallel along the polymer backbone, with the Zn atoms being separated by 14.3 Å. The polymers are organized in a parallel and offset fashion such that nearest-neighbour C=C bonds of the olefins are separated by 9.09 Å. The counter $ClO_4^-$ ions and included water molecules are located between the polymer strands and assemble with the µ-OH ions to form a 1D network held together by O—H . . . O hydrogen bonds. Similar to Complex 1, the network is composed of cyclic hydrogen-bonded arrays involving water molecules that bridge adjacent $ClO_4^-$ ions. This packing makes the C=C bonds of the 1D polymer the sole olefins of Complex 3 organized in the solid for [2+2] photoreaction.

Example 5

Preparation of Representative Complex of the Invention (Complex 4)—Irradiation of Complex 3 to provide Complex 4

UV-irradiation of a powdered crystalline sample of Complex 3 (broadband Hg-lamp) for a period of 32 hours produced the corresponding cyclobutane containing adduct Complex 4 in 95% yield. The formation of Complex 4 was evidenced by a near complete disappearance of the olefinic singlet at 7.54 ppm and the appearance of a singlet at 4.66 ppm (solvent: DMSO-d$_6$). The latter peak is consistent with the rctt stereochemistry of the cyclobutane ring of Complex 4. A thermogravimetric analysis revealed that the solid lost approximately half (i.e. two) of the included H$_2$O molecules during the photoreaction. The loss of the H$_2$O was accompanied by a loss of crystallinity, as demonstrated by powder X-ray diffraction data. Single crystals of Complex 3 also turn opaque during the photoreaction which is in contrast to Complex 1.

Example 6

Preparation of Representative Complexes of the Invention (Complexes 5-9)

As detailed below, complexes of the invention (5, 6, 7, 8, and 9) were prepared having the following structure:

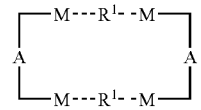

wherein: each group MAM is a Schiff-base complex of formula 5', 6', 7', 8', or 9' (see below); each M is Zn; and each R$^1$ is trans-1,2-bis(4-pyridyl)ethylene).

Using a procedure similar to that described in Example 1, except replacing the 2-hydroxy-5-methyl-isophthalaldehyde used therein with the requisite dialdehyde (and for complex 9' replacing the 2-aminoethyl-pyridine used in Example 1 with 2-aminomethyl-pyridine), the following Schiff-base complexes 5'-9' of the formula:

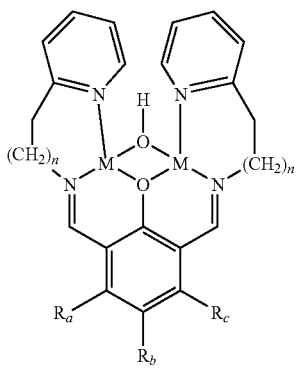

were prepared.

| Complex | $R_a$ | $R_b$ | $R_c$ | N |
|---|---|---|---|---|
| 5' | H | —C(CH$_3$)$_3$ | H | 1 |
| 6' | H | —CH$_2$Ph | H | 1 |
| 7' | H | —OCH$_3$ | H | 1 |
| 8' | H | Br | H | 1 |
| 9' | H | —C(CH$_3$)$_3$ | H | 0 |

Diffusion of a MeOH solution (10 mL) of trans-1,2-bis(4-pyridyl)ethylene) (4,4'-bpe) into an aqueous solution of Zn(II), Li(I), and one of the Schiff-base complexes (5', 6', 7', 8', or 9') resulted in precipitation of crystals of a complex of the invention (5, 6, 7, 8, or 9) The structure of each complex 5-9 of the invention was confirmed by X-ray crystal analysis.

The intermediate dialdehydes used for the synthesis of Complexes 5-9 were prepared from the corresponding 4-substituted phenols using a procedure similar to that described by Lindroy L. F., et al., *Synthesis*, 1998, 1029.

Example 7

Preparation of Representative Complex of the Invention (Complex 10)

Using a procedure similar to that described in Example 2, Complex 7 was irradiated to provide the corresponding cyclobutane containing complex of the invention, Complex 10. The structure of Complex 10 was confirmed by X-ray crystal analysis.

Example 8

Preparation of Representative Complexes of the Invention (Complex 11 and 12)

Using a procedure similar to that described in Example 6, except replacing the Schiff-Base complex 5' used therein with the corresponding Schiff-Base complex wherein $R_b$ is carboxy or ethyl, complexes of the invention can be prepared wherein $R_b$ is carboxy (11) or ethyl (12).

Example 9

Preparation of Representative Complexes of the Invention (Complex 13 and 14)

Using a procedure similar to that described in Example 6, except replacing the Schiff-Base complex 9' used therein with the corresponding Schiff-Base complex wherein $R_b$ is carboxy or ethyl, complexes of the invention can be prepared wherein $R_b$ is carboxy (13) or ethyl (14).

Example 10

Preparation of Representative Complexes of the Invention (15, 16, 17, 18, 19, 20, 21 and 22)

Using a procedure similar to that described in Example 2, complexes 5, 6, 8, 9, 11, 12, 13 or 14 can be irradiated to provide the corresponding cyclobutane containing complex of the invention, complex 15, 16, 17, 18, 19, 20, 21 or 22, respectively.

All publications, patents, and patent documents are incorporated by reference herein, as though individually incorporated by reference. The invention has been described with reference to various specific and preferred embodiments and techniques. However, it should be understood that many variations and modifications may be made while remaining within the spirit and scope of the invention.

What is claimed is:

1. A metal-organic complex comprising two or more metal atoms wherein one metal atom is associated with a first organic group comprising one or more double bonds and another metal atom is associated with a second organic group comprising one or more double bonds such that one or more double bonds in the first organic group are spatially oriented to react with one or more double bonds in the second organic group.

2. The complex of claim 1 that comprises the following structure:

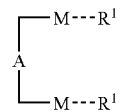

wherein:

the group MAM is a metal-organic group comprising at least two metal atoms M;

each $R^1$ is independently an organic group comprising one or more double bonds; and the dashed lines designate an association between $R^1$ and M.

3. A metal-organic complex comprising two or more metal atoms wherein one metal atom is associated with a first organic group comprising one or more double bonds and another metal atom is associated with a second organic group comprising one or more double bonds such that one or more double bonds in the first organic group are spatially oriented to react with one or more double bonds in the second organic group wherein each metal atom is independently Zn.

4. The complex of claim 2 wherein each group MAM is a Schiff-base complex.

5. A metal-organic complex comprising two or more metal atoms wherein one metal atom is associated with a first organic group comprising one or more double bonds and another metal atom is associated with a second organic group comprising one or more double bonds such that one or more double bonds in the first organic group are spatially oriented to react with one or more double bonds in the second organic group wherein the complex comprises the following structure:

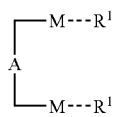

wherein:
the group MAM is a metal-organic group comprising at least two metal atoms M; each $R^1$ is independently an organic group comprising one or more double bonds; and the dashed lines designate an association between $R^1$ and M;
wherein each group MAM is a Schiff-base complex and wherein one or more of the groups MAM has the following structure:

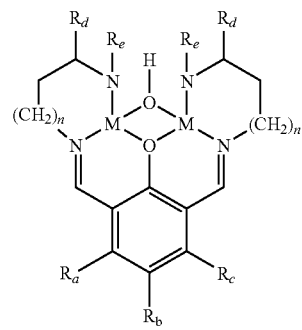

wherein:
each $R_a$, $R_b$, and $R_c$ is independently hydrogen, halo, nitro, cyano, $C_{1-6}$alkyl, $C_{1-6}$alkoxy, $C_{1-6}$alkanoyl, $C_{1-6}$alkanoyloxy, $C_{1-6}$alkoxycarbonyl, trifluoromethyl, aryl ($C_{1-6}$alkyl), carboxy, or trifluoromethoxy;
each n is independently 0, 1, 2, or 3; and
each $R_d$ and $R_e$ is independently hydrogen or $C_{1-6}$alkyl; or $R_d$ and $R_e$ together with the atoms to which they are attached form a 5, 6, 7, or 8 membered saturated or unsaturated ring.

6. The complex of claim 5 wherein $R_b$ is $C_{1-6}$alkyl, benzyl, bromo, or $C_{1-6}$alkoxy.

7. The complex of claim 1 which is a crystalline solid.

* * * * *

UNITED STATES PATENT AND TRADEMARK OFFICE
CERTIFICATE OF CORRECTION

| | | |
|---|---|---|
| PATENT NO. | : 7,772,416 B2 | Page 1 of 1 |
| APPLICATION NO. | : 11/150587 | |
| DATED | : August 10, 2010 | |
| INVENTOR(S) | : Leonard R. MacGillivray | |

It is certified that error appears in the above-identified patent and that said Letters Patent is hereby corrected as shown below:

Title Page,
Below Related U.S. Application Data section, "(60) Provisional application No. 60/578,781, filed on Jun. 10, 2004" insert priority claim: --International Patent Application No. PCT/US2004/033295, filed on Oct. 8, 2004.--

Column 1, GOVERNMENT FUNDING section, lines 15-16, delete the words "may have" and replace with --has--, so the sentence reads as follows:

The United States Government has certain rights in the invention.

Signed and Sealed this
Eighth Day of March, 2011

David J. Kappos
*Director of the United States Patent and Trademark Office*